United States Patent
Kühnle et al.

(10) Patent No.: US 6,184,417 B1
(45) Date of Patent: Feb. 6, 2001

(54) METHOD FOR PREPARING ACETOPHENONES WITH A FLUORALKYL-SUBSTITUTED AROMATIC NUCLEUS

(75) Inventors: Wulf Kühnle, Köln; Albrecht Marhold, Leverkusen; Guido Steffan, Odenthal, all of (DE)

(73) Assignee: Bayer Aktiengesellschaft, Leverkusen (DE)

( * ) Notice: Under 35 U.S.C. 154(b), the term of this patent shall be extended for 0 days.

(21) Appl. No.: 09/403,962

(22) PCT Filed: Apr. 23, 1998

(86) PCT No.: PCT/EP98/02410

§ 371 Date: Nov. 1, 1999

§ 102(e) Date: Nov. 1, 1999

(87) PCT Pub. No.: WO98/50335

PCT Pub. Date: Nov. 12, 1998

(30) Foreign Application Priority Data

May 6, 1997 (DE) ............................................. 197 19 054

(51) Int. Cl.⁷ ............................. C07C 45/00; C07C 49/78
(52) U.S. Cl. ............................................. 568/309; 568/335
(58) Field of Search ...................................... 568/309, 335

(56) References Cited

U.S. PATENT DOCUMENTS 4,143,166   3/1979   Takaya et al. ........................ 424/246

OTHER PUBLICATIONS

Research Disclosure, XP 000726840, p. 706, 1997.*
Beech et al, Journal of the Chemical Society, pp. 1297–1302, 1954.*
Liebigs Ann. Chem. 717, pp. 80–90 1968, Umsetzungen von o–und m–Trifluormethyl–benzaldehyd mit Diazomethan und –äthan, von Bernd Eistert et al.
J. Am. Chem. Soc. 68, pp. 736–738, 1946, The Preparation and Polymerization of Some Substituted Styrenes, C.S. Marvel et al.
Jouranl of Organometallic Chemistry, 489, 1995, pp. 137–143, Electrosynthesis of (trifluoromethyl) copper complexes from bromotrifluoromethane: reactivities with various organic halides, J. M. Paratian et al, 489, 137–143 (1995).

* cited by examiner

*Primary Examiner*—Sreeni Padmanabhan
(74) *Attorney, Agent, or Firm*—Joseph C. Gil; Diderico van Eyl

(57) ABSTRACT

Acetophenones which are substituted on the aromatic ring by fluoroalkyl are prepared in a particularly advantageous, environmentally friendly and effective manner from fluoroalkylanilines and acetaldoxime by preparing from a fluoroalkylaniline a corresponding diazonium salt solution, and reacting this with acetaldoxime in the presence of at least one copper compound, without adding any buffer salts or reducing agents, carrying out the reaction at from 20 to 50° C. and in the presence of halide ions and subsequently heating to a temperature in the range from 70 to 110° C.

9 Claims, No Drawings

METHOD FOR PREPARING ACETOPHENONES WITH A FLUORALKYL-SUBSTITUTED AROMATIC NUCLEUS

This is the U.S. National Stage Application of PCT/EP98/02410 filed Apr. 23, 1998.

BACKGROUND OF THE INVENTION

The present invention relates to an improved process for preparing acetophenones which are substituted on the aromatic ring by fluoroalkyl. Such compounds are useful intermediates for preparing antibacterial agents (see DE-A 26 04 207).

A known process for preparing trifluoromethylacetophenone on an industrial scale involves the preparation, from trifluoromethylaniline and sodium nitrite in the presence of hydrochloric acid, of the corresponding diazonium salt solution, which is then buffered with sodium acetate and added, at from 5 to 15° C., to an initial charge comprising water, acetaldoxime, a copper(II) salt, a reducing agent (sodium thiosulphate) and a large amount of sodium acetate buffer. For work-up, hydrochloric acid is added and the mixture is heated to reflux, subjected to steam distillation and extracted, and the distillate is dried, the extracting agent is stripped off and the residue is distilled under reduced pressure. Based on the fluoromethylaniline employed, this gives trifluoromethylacetophenone in a yield of 33% of theory (see DE-A 26 04 207, Preparation Example 1.4).

In addition to the low yield, this process has the disadvantage that large amounts of auxiliaries, for example buffer salts, reducing agents and hydrochloric acid, are used which render work-up more difficult, result in a considerable salt load of the waste water and, after they have been separated off, cause great costs for an environmentally safe disposal.

Other known processes for preparing trifluoromethylacetophenone (see, for example, Liebigs Ann. Chem. 717, 80–90 (1968), J.Am. Chem. Soc. 68, 736 (1946), J. Organomet. Chem. 489, (1–2), 137–143 (1995)) are not suitable to be employed on an industrial scale because they require apparatus and reagents which are expensive and difficult to handle.

DESCRIPTION OF THE INVENTION

We have now found a process for preparing acetophenones which are substituted on the aromatic ring by fluoroalkyl from fluoroalkylanilines and acetaldoxime, in which from a fluoroalkylaniline a corresponding diazonium salt solution is prepared which is reacted with acetaldoxime in the presence of at least one copper compound, characterized in that no buffer salts and no reducing agents are added, the reaction is carried out at from 20 to 50° C. and in the presence of halide ions and the mixture is subsequently heated to a temperature in the range from 70 to 110° C.

For the process according to the invention, it is possible to employ, for example, fluoroalkylanilines of the formula (I)

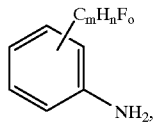

(I)

in which
  m represents 1, 2 or 3,
  n represents (2m+1)–o and
  o represents (2m+1)–n.

In the formula (I), n preferably represents zero and o preferably represents (2m+1). The $C_mH_nF_o$ group is preferably in the 3-position to the amino group. Particular preference is given to using 3-trifluoromethylaniline.

The preparation of the diazonium salt solution can be carried out in a customary manner, for example by reaction with sodium nitrite in the presence of a strong inorganic acid at from 0 to –15° C. It is an essential feature of the present invention that the finished diazonium salt solution is not admixed with any buffer salts, for example sodium acetate.

Based on 1 mole of fluoroalkylaniline employed, it is possible to use, for example, from 1 to 2 mol, preferably from 1.2 to 1.6, of acetaldoxime.

Suitable copper compounds are, for example, salts and complex compounds in which the copper is present in the oxidation state +1 or +2. Examples of salts are halides and sulphates, examples of complex compounds are those with hydroxylamine or acetaldoxime ligands. The copper compounds may contain water. Specific examples are $CuSO_4$, $CuSO_4 \times 5H_2O$, CuCl, CuBr, $CuCl_2$, $CuBr_2$, Cu(O—N=CH—CH_3) and $Cu(O—N=CH—CH_3)_2$. Based on 1 mole of fluoroalkylaniline employed, it is possible to use, for example, from 0.04 to 0.2 mol, preferably from 0.045 to 0.1 mol, of one or more copper compounds.

The process according to the invention can be carried out in different ways. For example, a mixture of acetaldoxime, copper compound(s) and a little water is initially charged and the diazonium salt solution is metered in. It is also possible to prepare, for example, initially the diazonium salt solution, which is then metered into an aqueous solution of one or more copper compounds which had been charged initially, and the resulting mixture is metered into acetaldoxime which had been charged initially.

It is an essential feature of the present invention that prior to or during the reaction of the diazonium salt solution with acetaldoxime no buffer salts (such as sodium acetate) and no reducing agents (such as sodium thiosulphate) are added.

The reaction according to the invention is preferably carried out at from 25 to 45° C.

The presence of halide ions during the reaction, which is required according to the invention, can be achieved in the most simple case by using as strong inorganic acid for the preparation of the diazonium salt solution a hydrohalic acid, for example from 25 to 40% by weight strength aqueous hydrochloric acid or from 25% by weight strength aqueous hydrobromic acid. If it is intended to use another strong inorganic acid in the preparation of the diazonium salt solution, this is possible, but in this case halide ions have to be added in another manner, for example in the form of metal halide, such as in the form of NaCl or KBr. Based on 1 mole of copper compounds, for example, at least 1 mole, preferably at least 10 mol, of halide ions are present in the reaction mixture.

During the metered addition of the diazonium salt solution to the acetaldoxime, it is advantageous to ensure that the reaction mixture is mixed intensively, for example by means of a vibration or a dispersion apparatus of the Ultra-Turrax® type.

When preparing the components to be reacted with one another, and during the reaction, it is furthermore advantageous to substantially exclude the presence of oxygen. To this end, it is possible, for example, to work in a nitrogen atmosphere, to introduce nitrogen into the reaction mixtures and/or components to be handled or to apply a slight vacuum for degassing.

After the diazonium salt solution and the acetaldoxime component have been admixed completely, the reaction mixture may be allowed, if appropriate, to react for some more time, for example for from 15 minutes to 1 hour, at temperatures in the range of from 20 to 50° C.

It is not necessary to admix (more) hydrochloric acid before work-up.

If the fully reacted reaction mixture is worked up by steam distillation, no particular attention should be paid to the subsequent heating to from 70 to 110° C., preferably from 80 to 105° C., since the mixture has to be heated to temperatures in this range in any case. If work-up is to be carried out in a different way, for example by extraction, heating to from 70 to 110° C. has to be carried out beforehand separately, for example for from 5 to 30 minutes.

The crude acetophenones which are substituted at the aromatic ring by fluoroalkyl and which are present after work-up, for example by steam distillation or extraction, can be purified further by fractional distillation, for example over a column.

Thus, it is possible to obtain the desired products in purities of more than 98% and in yields of from 48 to more than 55% of theory.

If a fluoroalkylaniline of the formula (I) has been employed, the corresponding product of the formula

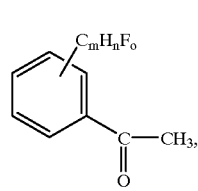

(II)

in which the symbols used have the meaning given under formula (I) is obtained.

Even though the process according to the invention, in contrast to the prior art, does not require the addition of buffer salts and reducing agents and can be carried out with lower amounts of strong inorganic acids and copper compounds, its yield of target products is generally increased by at least 50% (relative). This is particularly surprising and renders the process according to the invention considerably more efficient than the known processes. The amounts of waste water and their salt contents are considerably lower, and even the space yield is strongly increased. Because of the reaction temperature of the invention, which is increased compared to the prior art, an increase of decomposition reactions was to be expected; however, this is not the case.

The invention is further described in the following illustrative examples in which all parts and percentages are by weight unless otherwise indicated.

EXAMPLES

Example 1

Under nitrogen, 1290 g of water and 740 g of hydrochloric acid (30% by weight strength) were initially charged and cooled to from −10 to −5° C. At below −5° C., 334 g of 3-aminobenzotrifluoride were then metered in (content 99.9%). 149 g of sodium nitrite were dissolved in 690 g of water and metered in at below 0° C. over the course of 2 hours. The mixture was then stirred for another 1 hour. Under nitrogen, an initial charge of 24 g of copper sulphate hydrate, 73 g of water and 183 g of acetaldoxime was heated to 28° C., and the diazonium salt solution which had been prepared beforehand was metered in with intensive stirring over the course of 2 hours. The mixture was allowed to react at 30° C. for another 30 minutes. After 1 hour, the mixture was heated to 100° C. and the crude product was distilled off together with water. After the removal of the water from the distillate, the crude product was distilled over a column. 202 g of 3-trifluoromethylacetophenone were obtained (content according to GC 99.1%). This corresponds to a yield of 51.5% of theory.

Example 2

A diazonium salt solution was prepared as described in Example 1. An initial charge of 0.53 parts by weight (based on 3-trifluoromethylaniline) of acetaldoxime and 0.073 parts by weight (based on 3-trifluoromethylaniline) of copper(II) salt of the acetaldoxime was degassed of oxygen by passing through nitrogen and heated to 40° C. Over a period of 1.5 hours, the diazonium salt solution was added dropwise. The mixture was subsequently heated to 100° C. and the crude product was distilled off together with water. After phase separation and purificative distillation over a column, 3-trifluoromethylacetophenone was obtained in a yield of 56% of theory.

Example 3

Under nitrogen, 297 g of water and 246 g of hydrobromic acid (48% strength) were initially charged, and 80 g of 3-trifluoromethylaniline were introduced. The suspension that formed was stirred and cooled to −6° C. Over a period of 30 minutes, 37 g of sodium nitrite dissolved in 78 g of water were now added dropwise, and the mixture was stirred for another 30 minutes. The solution that had formed was subsequently, at 30° C., metered into an initial charge of 6 g of copper sulphate pentahydrate dissolved in 26 g of water. This mixture was now added dropwise over a period of 1.5 hours to an initial charge of 45 g of acetaldoxime, the temperature being controlled in such a manner that it did not exceed 40° C. The mixture was subsequently heated to 100° C. The crude product was distilled off together with water. After the water had been removed from the distillate, the crude product was distilled over a column. 44 g (=48% of theory) of 3-trifluoromethylacetophenone were obtained.

Although the present invention has been described in detail with reference to certain preferred versions thereof, other variations are possible. Therefore, the spirit and scope of the appended claims should not be limited to the description of the versions contained therein.

What is claimed is:

1. Process for preparing acetophenones which are substituted on the aromatic ring by fluoroalkyl from fluoroalkylanilines and acetaldoxime, in which from a fluoroalkylaniline a corresponding diazonium salt solution is prepared the process comprising reacting the diazonium salt solution with acetaldoxime in the presence of at least one copper compound, wherein no buffer salts and no reducing agents are added, wherein the reaction is carried out at from 20 to 50° C. and in the presence of halide ions and the mixture is subsequently heated to a temperature in the range from 70 to 110° C.

2. Process according to claim 1, wherein fluoroalkylanilines of the formula (I) are employed

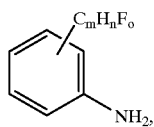

(I)

wherein
 m represents 1, 2 or 3,
 n represents (2m+1)−o and
 o represents (2m+1)−n.

3. Process according to claim 1, wherein the diazonium salt solution is carried out by reacting the fluoroalkylaniline with sodium nitrite in the presence of a strong inorganic acid at a temperature ranging from 0 to −15° C.

4. Process according to claim 1, wherein from 1 to 2 mol of acetaldoxime are employed per mole of fluoroalkylaniline used.

5. Process according to claim 1, wherein the copper compounds used are salts and/or complex compounds in which the copper is present in the oxidation state +1 or +2 and from 0.04 to 0.2 mol of one or more copper compounds are employed, based on 1 mole of fluoroalkylaniline employed.

6. Process according to claim 1, wherein the process is carried out by initially charging a mixture of acetaldoxime, copper compounds and a little water and the diazonium solution is metered in or the diazonium salt solution is prepared and metered into an aqueous solution of one or more copper compounds which had been charged initially, and the resulting mixture is metered into acetaldoxime which had been charged initially.

7. Process according to claim 1, wherein at least 1 mole of halide ions is present in the reaction mixture, based on 1 mole of copper compounds.

8. Process according to claim 1, wherein the presence of oxygen is substantially excluded during the preparation of the components to be reacted with one another during the reaction.

9. Process according to claim 1, wherein the reaction mixture is, after the reaction has ended, worked up by steam distillation or extraction and subsequent fractional distillation.

* * * * *